US00PP23886P2

(12) United States Plant Patent
Kinney

(10) Patent No.: US PP23,886 P2
(45) Date of Patent: Sep. 10, 2013

(54) CEDAR TREE NAMED 'MONKINN'

(50) Latin Name: *Cedrus deodara*
Varietal Denomination: Monkinn

(75) Inventor: Ron Damien Kinney, Dayton, OR (US)

(73) Assignee: Monrovia Nursery Company, Inc., Azusa, CA (US)

( * ) Notice: Subject to any disclaimer, the term of this patent is extended or adjusted under 35 U.S.C. 154(b) by 0 days.

(21) Appl. No.: 13/385,063

(22) Filed: Jan. 31, 2012

(51) Int. Cl.
*A01H 5/00* (2006.01)

(52) U.S. Cl.
USPC ..... Plt./213

(58) Field of Classification Search
USPC ..... Plt./213
See application file for complete search history.

*Primary Examiner* — Kent L Bell
(74) *Attorney, Agent, or Firm* — C. A. Whealy

(57) ABSTRACT

A new and distinct cultivar of Cedar tree named 'Monkinn', characterized by its compact and low spreading plant habit; relatively slow-growing growth habit; freely branching habit, dense and bushy plant form; young leaves that are greyed yellow in color becoming golden yellow with development and maintaining the golden yellow coloration throughout the winter; and leaves that are resistant to sun-burning.

1 Drawing Sheet

Botanical designation: *Cedrus deodara.*
Cultivar denomination: 'MONKINN'.

BACKGROUND OF THE INVENTION

The present Invention relates to a new and distinct cultivar of Cedar tree, botanically known as *Cedrus deodara*, and hereinafter referred to by the name 'Monkinn'.

The new Cedar tree is a naturally-occurring whole plant mutation of *Cedrus deodara* 'Feelin Blue', not patented. The new Cedar tree was discovered and selected by the Inventor as a single tree during the spring of 2004 within a population of trees of 'Feelin Blue' in a controlled outdoor nursery environment in Dayton, Oreg.

Asexual reproduction of the new Cedar tree by grafting in a controlled environment in Dayton, Oreg. since December 2006 has shown that the unique features of this new Cedar tree are stable and reproduced true to type in successive generations.

SUMMARY OF THE INVENTION

Trees of the new Cedar have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Monkinn'. These characteristics in combination distinguish 'Monkinn' as a new and distinct Cedar tree:

1. Compact and low spreading plant habit.
2. Relatively slow-growing growth habit.
3. Freely branching habit, dense and bushy plant form.
4. Young leaves that are greyed yellow in color becoming golden yellow with development and maintaining the golden yellow coloration throughout the winter.
5. Leaves that are resistant to sun-burning.

Trees of the new Cedar are most similar to trees of the parent, 'Feelin Blue'. In side-by-side comparison, trees of the new Cedar differ primarily from trees of 'Feelin Blue' in leaf coloration as trees of 'Feelin Blue' have greyish blue-colored leaves.

Trees of the new Cedar can also be compared to trees *of Cedrus deodara* 'Golden Horizon', not patented. Trees of the new Cedar differ from trees of 'Golden Horizon' in the following characteristics:

1. Trees of the new Cedar are low spreading and are not as mounding as trees of 'Golden Horizon'.
2. Trees of the new Cedar are slower growing and more compact than plants of 'Golden Horizon'.
3. Trees of the new Cedar and 'Golden Horizon' differ in leaf color as fully expanded leaves of plants of 'Golden Horizon' are yellow green in color.

BRIEF DESCRIPTION OF THE PHOTOGRAPHS

The accompanying colored photographs illustrate the overall appearance of the new Cedar tree showing the colors as true as it is reasonably possible to obtain in colored reproductions of this type. Colors in the photographs may differ slightly from the color values cited in the detailed botanical description which accurately describe the colors of the new Cedar tree.

The photograph at the top of the sheet is a side perspective view of a typical tree of 'Monkinn' grown in a container.

The photograph at the bottom of the sheet is a close-up view of typical branches of 'Monkinn'.

DETAILED BOTANICAL DESCRIPTION

Trees used for the aforementioned photographs and following observations and measurements were grown in five-gallon containers in Dayton, Oreg. during the autumn and winter in an outdoor nursery and under conditions which approximate commercial Cedar tree production. During the production of the trees, day temperatures ranged from 4° C. to 32° C. and night temperatures ranged from −2° C. to 15° C. Trees were 25 months old when the photographs and description were taken. In the following description, color references are made to The Royal Horticultural Society Colour Chart, 2007 Edition, except where general terms of ordinary dictionary significance are used.

Botanical classification: *Cedrus deodara* 'Monkinn'.

Parentage: Naturally-occurring whole plant mutation of *Cedrus deodara* 'Feelin Blue', not patented.

Propagation:

*Type*.—By grafting.

Plant description:

*Plant and growth habit*.—Compact and low spreading evergreen shrub, rounded plant habit; relatively slow-growing growth habit.

*Branching habit*.—Freely branching with about twelve lateral branches developing per plant; dense and bushy plant form; trees maintain their lower branches and foliage at the soil level.

*Plant height*.—About 62 cm.

*Plant diameter*.—About 65 cm.

*Trunk diameter at soil level*.—About 2.4 cm.

*Lateral branch description*.—Length: About 36 cm. Diameter: About 1.1 cm. Internode length: About 2.8 mm. Texture: Young branches: Densely pubescent. Mature branches: Woody, rough. Strength: Strong. Aspect: Upright to pendulous. Color: Young branches: Close to 156B, becoming closer to 148A with development. Mature branches: Close to N199A.

*Leaf description*.—Arrangement: Whorled to alternate becoming fascicled on older branches. Length: About 2.3 cm; within fascicles, about 1.5 cm. Width: About 1 mm. Shape: Acicular. Apex: Apiculate. Base: Truncate. Margin: Entire. Texture, upper and lower surface: Smooth, glabrous; stiff. Venation pattern: Parallel. Color: Developing leaves, upper and lower surfaces: Close to 161C. Fully expanded leaves, upper surface: Close to 153A; venation, close to 138A; golden color maintained throughout the winter; leaves resistant to sun-burning. Fully expanded leaves, lower surface: Close to 146B; venation, close to 138A. Petioles: Length: About 1 mm. Diameter: About 1 mm. Texture, upper and lower surfaces: Smooth, glabrous. Color, upper surface: Close to 165C. Color, lower surface: Close to 164D.

*Cone description*.—Cone development has not been observed on trees of the new Cedar.

Disease & pest resistance: Trees of the new Cedar have not been noted to be resistant to pathogens or pests common to Cedar trees.

Weather tolerance: Trees of the new Cedar tree have been observed to be tolerant to drought, rain and wind. Trees of the new Cedar are hardy to USDA Hardiness Zones 7 to 9.

It is claimed:

1. A new and distinct Cedar tree named 'Monkinn' as illustrated and described.

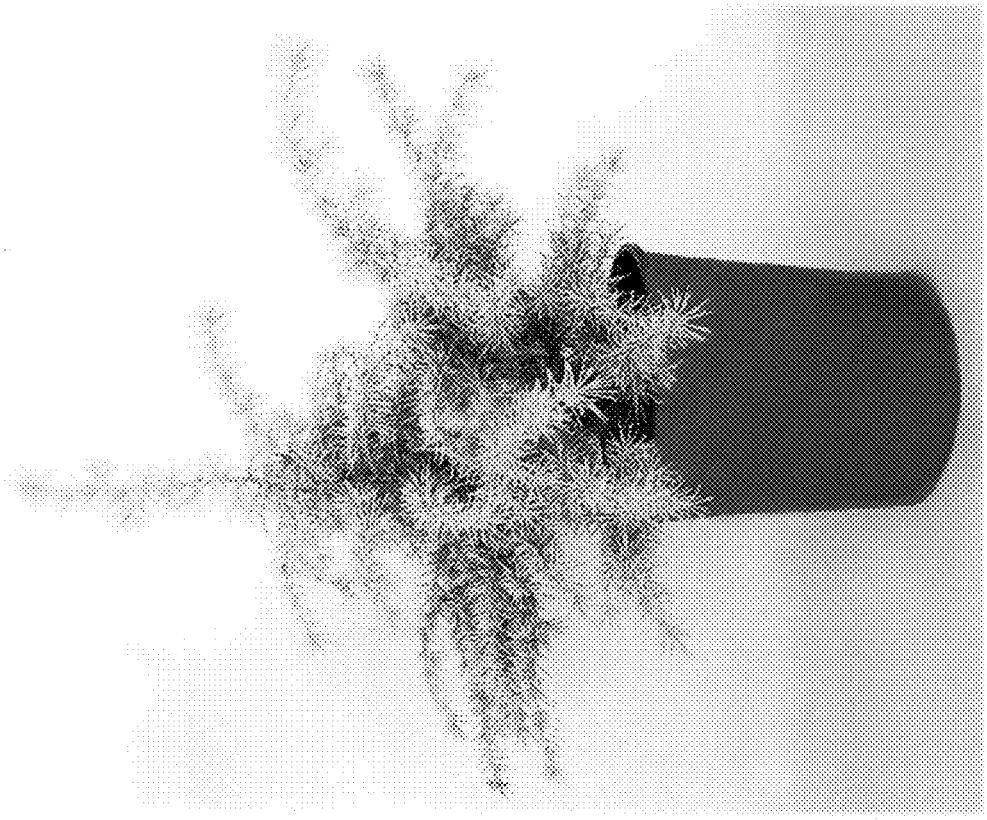
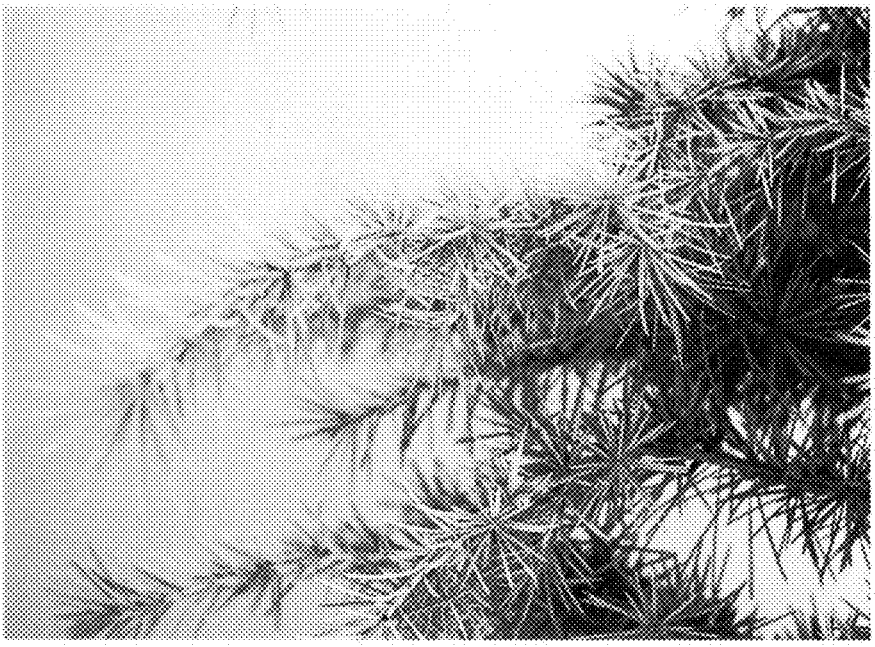

* * * * *